(12) United States Patent
Karra et al.

(10) Patent No.: US 10,967,977 B2
(45) Date of Patent: Apr. 6, 2021

(54) AIRCRAFT AIR SUPPLY AND CONTAMINANT DETECTION SYSTEM

(71) Applicant: Hamilton Sundstrand Corporation, Charlotte, NC (US)

(72) Inventors: Jagadeswara Reddy Karra, Ellington, CT (US); Zissis A. Dardas, Worcester, MA (US); Peter R. Harris, West Hartford, CT (US)

(73) Assignee: HAMILTON SUNSTRAND CORPORATION, Charlotte, NC (US)

( * ) Notice: Subject to any disclaimer, the term of this patent is extended or adjusted under 35 U.S.C. 154(b) by 181 days.

(21) Appl. No.: 16/028,999

(22) Filed: Jul. 6, 2018

(65) Prior Publication Data

US 2020/0010201 A1    Jan. 9, 2020

(51) Int. Cl.
| | |
|---|---|
| *B01D 53/02* | (2006.01) |
| *B64D 13/06* | (2006.01) |
| *B01D 53/04* | (2006.01) |
| *B01D 53/30* | (2006.01) |
| *B64D 13/02* | (2006.01) |

(Continued)

(52) U.S. Cl.
CPC .............. *B64D 13/06* (2013.01); *B01D 53/04* (2013.01); *B01D 53/30* (2013.01); *B64D 13/02* (2013.01); *G01N 31/224* (2013.01); *G01N 33/0004* (2013.01); *B01D 2253/204* (2013.01); *B01D 2257/556* (2013.01); *B01D 2259/4009* (2013.01); *B01D 2259/4575* (2013.01); *B64D 2013/0651* (2013.01)

(58) Field of Classification Search
CPC ........ B01D 2253/204; B01D 2257/556; B01D 2259/4009; B01D 2259/4575; B01D 53/04; B01D 53/30; B64D 13/02; B64D 13/06; G01N 21/552; G01N 21/7703
See application file for complete search history.

(56) References Cited

U.S. PATENT DOCUMENTS

| | | |
|---|---|---|
| 9,902,499 B2 | 2/2018 | Fox et al. |
| 2016/0231233 A1 | 8/2016 | Wang et al. |

(Continued)

FOREIGN PATENT DOCUMENTS

WO     2016183044 A1    11/2016

OTHER PUBLICATIONS

European Search Report Issued in European Application No. 19184662.5 dated Nov. 19, 2019; 6 Pages.

(Continued)

*Primary Examiner* — Christopher P Jones
(74) *Attorney, Agent, or Firm* — Cantor Colburn LLP

(57) ABSTRACT

An aircraft pressurized air system and method is disclosed. The system includes a compressor that receives and compresses outside air, and an air cycle machine that receives compressed air from the compressor and directs conditioned air to an aircraft pressurized zone. The system also includes a contaminant sensor disposed along an air flow path between the compressor and the aircraft pressurized zone, comprising an optical guide, a metal organic framework on an exterior surface of the optical guide in operative fluid communication with air from the air flow path, a light source in communication with the optical guide at a first end of the optical guide, and a light detector in communication with the optical guide at a second end of the optical guide.

16 Claims, 3 Drawing Sheets

(51) Int. Cl.
    *G01N 31/22*      (2006.01)
    *G01N 33/00*      (2006.01)

(56) References Cited

U.S. PATENT DOCUMENTS

| | | |
|---|---|---|
| 2018/0188166 A1 | 7/2018 | Zeller et al. |
| 2018/0188766 A1 | 7/2018 | Fryer |
| 2018/0243689 A1* | 8/2018 | Langer .................. B01J 20/22 |

OTHER PUBLICATIONS

Fang et al.; "Metal-Organic Framework-Based Sensors for Environmental Contaminant Sensing"; Nano-Micro Lett.; 2018; 19 Pages.

Chong, X. et al., "Ultrashort Near-Infrared Fiber-Optic Sensors for Carbon Dioxide Detection", Institute of Electrical and Electronics Engineers, 2015, p. 1-7.

J. Hromadka, et al., "Optical fibre long period grating gas sensor modified with metal organic framework thin films", Sensors and Actuators, 2015, p. 1-10.

L. E. Kreno, et al., "Metal!Organic Framework Materials as Chemical Sensors", Chemical Reviews, ACS Publications, 2011,p. 1-21.

X. Chong, et al., "Nearinfrared absorption gas sensing with metalorganic framework on optical fibers", Sensors and Acuators, Elsevier, 2016, p. 1-9.

Batten, et al. "Terminology of metal—organic frameworks and coordination (IUPAC Recommendations 2013)". Pure Appl. Chem., vol. 85, No. 8, pp. 1715-1724, 2013. (Jul. 29, 2013).

G.K. Vertelov et al., "TCP Electrochemical Detection"; ECS Transaction, vol. 3, No. 10, 2006, 15 pages.

Ki-Joong Kim et al., "Metal-Organic Framework Thin Film Coated Optical Fiber Sensors: A Novel Waveguide-Based Chemical Sensing Platform" ACS Sensors, vol. 3, 2018, 9 pages.

\* cited by examiner

AIRCRAFT AIR SUPPLY AND CONTAMINANT DETECTION SYSTEM

BACKGROUND

This disclosure relates to aircraft and on-board air supply systems, and more particularly to an on-board air delivery system with contaminant detection.

Aircraft equipped to fly at elevations above 10,000 feet can include an air supply system that supplies pressurized air to the aircraft cabin. Such systems generally draw a bleed of air from a compressor section of a gas turbine engine used for propulsion as a source of pressurized air, but can also utilize compressed air from other sources such as an electrically-powered compressor. The compressed air supply can be subject to further conditioning such as in an air cycle machine in which the compressed air can be cooled, subjected to one or more compression and expansion steps by turbine and compressor blades on a shared rotary power connection, and dried before delivery to a cabin air recirculation loop. As with any occupied enclosed conditioned air space, it is desirable to maintain an acceptable air quality, and air treatment processes such as ozone removal and various types of filtration or other air quality treatments have been used or proposed. However, testing for contaminants can be challenging in an aircraft environment where conditions can be adverse and performance specifications can be demanding.

BRIEF DESCRIPTION

An aircraft pressurized air system is disclosed. The system includes a compressor that receives and compresses outside air, and an air cycle machine that receives compressed air from the compressor and directs conditioned air to an aircraft pressurized zone. The system also includes a contaminant sensor disposed along an air flow path between the compressor and the aircraft pressurized zone, comprising an optical guide, a metal organic framework on an exterior surface of the optical guide in operative fluid communication with air from the air flow path, a light source in communication with the optical guide at a first end of the optical guide, and a light detector in communication with the optical guide at a second end of the optical guide.

Also disclosed is a method of providing pressurized air to an aircraft pressurized zone. The method includes compressing outside air, and directing compressed outside air to an air cycle machine that receives conditioned air for delivery to the aircraft pressurized zone. The method further includes testing air on an air flow path between the compressor and the aircraft pressurized zone with a sensor comprising an optical guide, a metal organic framework on an exterior surface of the optical guide in operative fluid communication with air from the air flow path, a light source in communication with the optical guide at a first end of the optical guide, and a light detector in communication with the optical guide at a second end of the optical guide. In some embodiments, the method further includes generating a response based on detection of a contaminant. In some embodiments, the response is selected from: providing a system alarm to the presence of the contaminant, reducing a flow rate of compressed outside air to the air cycle machine, or increasing a recirculation flow rate in the aircraft pressurized zone.

In either of the foregoing embodiments, the metal organic framework can be configured to adsorb tricresyl phosphate.

Also disclosed is a method of testing for tricresyl phosphate. According to the method, light is directed from a light source to a light detector. A test gas is contacted with a metal organic framework on an exterior surface of an optical guide in communication with the light between the light source and the light detector, and a change is detected in light intensity or spectral properties of light received by the light detector caused by adsorption of tricresyl phosphate by the metal organic framework.

In any of the above embodiments, the optical guide can comprise a fiber optic element including a core comprising an optical material with a first refractive index, said metal organic framework on a first exterior surface portion of the core, and a cladding optically coupled to a second exterior surface portion of the core, said cladding comprising an optical material with a second refractive index lower than the first refractive index and configured to reflect light from the core at an interface between the core and the cladding.

In any one or combination of the foregoing embodiments, the first exterior surface portion can be disposed at a central portion along a length of the filament, and the cladding disposed on each side of the central portion along the length of the filament.

In any one or combination of the foregoing embodiments, the metal organic framework can include pore sizes greater than a molecular kinetic diameter of the tricresyl phosphate.

In any one or combination of the foregoing embodiments, the metal organic framework can include functional groups interactive with tricresyl phosphate.

In any one or combination of the foregoing embodiments, the metal organic framework can include pores larger than 1.5 nm.

In any one or combination of the foregoing embodiments, the metal organic framework can include polar functional groups.

In any one or combination of the foregoing embodiments, the system can further comprise a heat source in controllable thermal communication with the metal organic framework for regeneration.

In any one or combination of the foregoing embodiments, the system can further comprise a controller figured to detect a contaminant based on output from the contaminant sensor, and to generate a response thereto.

In any one or combination of the foregoing embodiments, the method can include, or the response generated by the controller can be selected from: providing a system alarm to the presence of the contaminant, reducing a flow rate of compressed outside air to the air cycle machine, increasing a recirculation flow rate in the aircraft pressurized zone, or activating an air contaminant removal protocol.

In any one or combination of the foregoing embodiments, the method can include, or the response generated by the controller can include regenerating the metal organic framework with heated air.

BRIEF DESCRIPTION OF THE DRAWINGS

Subject matter of this disclosure is particularly pointed out and distinctly claimed in the claims at the conclusion of the specification. The foregoing and other features, and advantages of the present disclosure are apparent from the following detailed description taken in conjunction with the accompanying drawings in which:

DETAILED DESCRIPTION

Figure 1A:
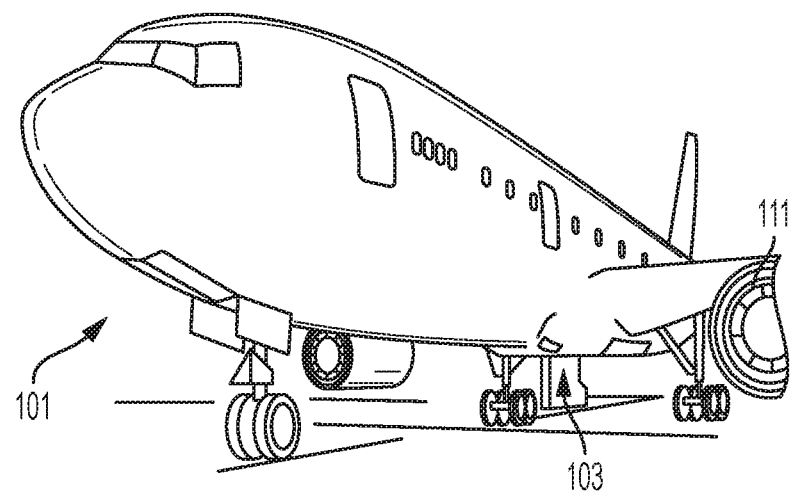
FIG. 1A is a schematic illustration of an aircraft that can incorporate various embodiments of the present disclosure.
Figure 1B:
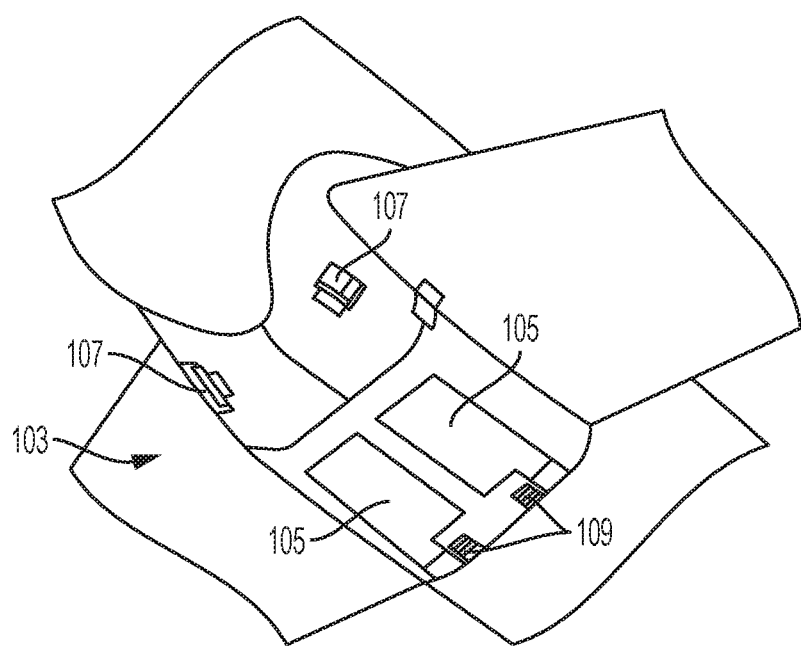
FIG. 1B is a schematic illustration of a bay section of the aircraft of FIG. 1A.

As shown in FIGS. 1A-1B, an aircraft includes an aircraft body 101, which can include one or more bays 103 beneath a center wing box. The bay 103 can contain and/or support one or more components of the aircraft 101. For example, in some configurations, the aircraft can include environmental control systems and/or fuel inerting systems within the bay 103. As shown in FIG. 1B, the bay 103 includes bay doors 105 that enable installation and access to one or more components (e.g., environmental control systems, fuel inerting systems, etc.). During operation of environmental control systems and/or fuel inerting systems of the aircraft, air that is external to the aircraft can flow into one or more ram air inlets 107. The outside air may then be directed to various system components (e.g., environmental conditioning system (ECS) heat exchangers) within the aircraft. Some air may be exhausted through one or more ram air exhaust outlets 109.

Also shown in FIG. 1A, the aircraft includes one or more engines 111. The engines 111 are typically mounted on wings of the aircraft and are connected to fuel tanks (not shown) in the wings, but may be located at other locations depending on the specific aircraft configuration. In some aircraft configurations, air can be bled from the engines 111 and supplied to environmental control systems and/or fuel inerting systems, as will be appreciated by those of skill in the art.

An aircraft environmental control system, also referred to as an ECS or ECS pack, can include customary components for air cycle cooling systems, including heat exchangers, compressors (e.g., turbine-blade compressors), turbines, and heat exchanger/water removal units. Air cycle cooling systems can be based on three-wheel architecture (a fan, a compressor, and a turbine) or four-wheel architecture (a fan, a compressor, and two turbines). In some embodiments, the ECS pack cools bleed air in a ram air heat exchanger, partially re-compresses it in a turbine-powered compressor, cools the partially re-compressed air in a second pass through the ram air heat exchanger, expands and further cools the air flow and removes water with a turbine in a flow loop with a heat exchanger water removal unit, and, in the case of a four-wheel architecture further expands and cools the air in a second turbine.

Figure 2:
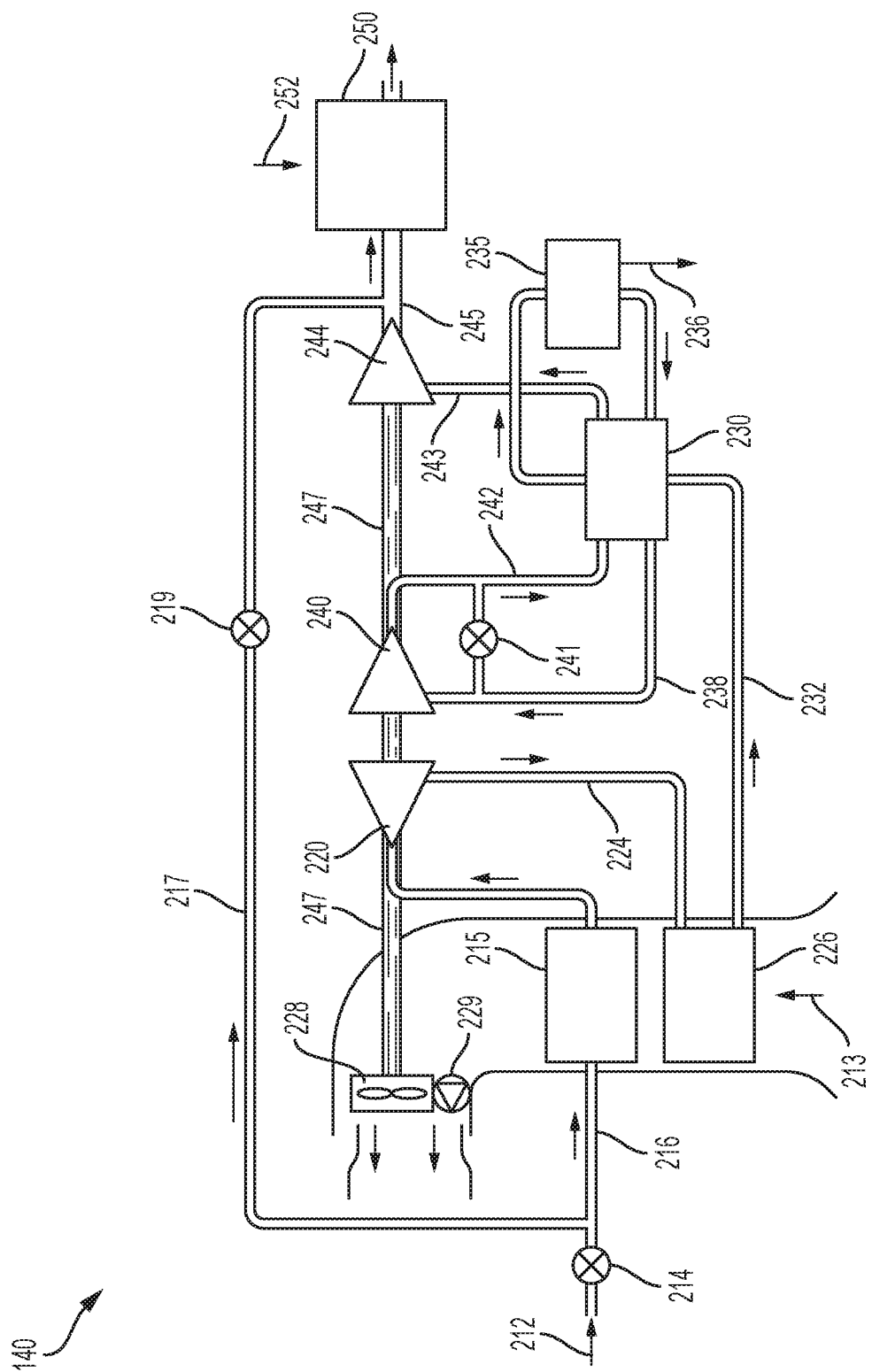
FIG. 2 is a schematic depiction of an example embodiment of an aircraft air cycle environmental conditioning system.

An example embodiment of on-board air cycle cooling system 140 is schematically shown in FIG. 2. Air cycle cooling system depicts a so-called "four-wheel" system, referring to the four rotating devices (a ram air fan, one compressor, and two turbines), but "three-wheel" systems having only a single turbine are also contemplated. As shown in FIG. 2, compressed air 212 from a compressed air source (not shown) such as a pre-cooled turbine engine bleed, an APU bleed, or an electrically-powered compressor is delivered through control valve 214. From there, the compressed air is directed to a heat exchanger 215 (also referred to in the art as a primary heat exchanger) where it rejects heat to ambient air flowing through or across a heat absorption side of heat exchanger 215. Cooled compressed air is discharged from heat exchanger 215 to compressor 220. A portion of the air going to heat exchanger 215 can be controllably diverted through conduit 217 and control/expansion valve 219 to mix with the outlet of turbine 244 and control the temperature of the conditioned air exiting the system. Compressor 220 compresses its portion of the air from the heat exchanger 215, which also results in heating of the air. The further compressed air is discharged from compressor 220 through conduit 224 to heat exchanger 226 (also referred to in the art as a secondary heat exchanger) where it rejects heat to ambient air flowing through or across a heat absorption side of heat exchanger 226.

The ambient air 213 flowing through or across the heat absorption sides of heat exchangers 215 and 226 can be a ram air flow from a forward-facing surface of the aircraft. In conditions under which insufficient airflow is generated by the forward motion of the aircraft for operation of the heat exchangers 215, 226, the air flow can be assisted by operation of fan 228. Check/bypass valve 229 allows for bypass of the fan 228 when ram air flow is sufficient for the needs of the heat exchangers 215 and 226. Heat exchangers 215 and 226 can share a flow path for the ambient cooling air, and can be integrated into a single unit with heat exchanger 215 sometimes referred to as a primary heat exchanger and heat exchanger 226 sometimes referred to as a secondary heat exchanger. Cooled air discharged from heat exchanger 226 is delivered through conduit 232 to a heat rejection side of heat exchanger 230. In the heat rejection side of heat exchanger 230, the air is further cooled to a temperature at or below the dew point of the air and flows into water removal unit 235 where liquid water 236 condensed from the air is removed. The dehumidified air flows through a heat absorption side of heat exchanger 230 where it is re-heated before being delivered through conduit 238 to turbine 240, where work is extracted as the air is expanded and cooled by turbine 240. A portion of the air going to turbine 240 can be diverted by valve 241 if needed to allow the temperature of the air at the inlet to the heat absorption side of heat exchanger 230 to be above freezing. The cooled expanded air discharged from the turbine 240 is delivered through conduit 242 to a heat absorption side of heat exchanger 230 where it along with the dehumidified air discharged from water collection unit 235 provides cooling needed to condense water vapor from air on the heat rejection side of heat exchanger 230. The air streams on the heat absorption side of the heat exchanger 230 are thus reheated. Heat exchanger 230 is also sometimes referred to as a condenser/reheater, and can be integrated with water removal unit 235 in a single unit. The reheated air from conduit 242 exiting from the heat absorption side of heat exchanger 230 flows through conduit 243 to turbine 244, where it is expanded and cooled, and then discharged from the system 140 through conduit 245 to mix manifold 250 where it is mixed with recirculating air 252 from the cabin or other pressurized zones before being discharged to back to the aircraft cabin or other pressurized zones of the aircraft. The environment air conditioning system 140 also includes a power transfer path 247 such as a rotating shaft that transfers power to the compressor 220 and fan 228 from work extracted by turbines 240 and 244.

As mentioned above, this disclosure includes a contaminant sensor disposed on an air flow path between a source of compressed air and pressurized zones of the aircraft such as the cabin, cockpit, cargo hold, and some equipment bays. Example locations of a contaminant sensor can include the ECS conduit 245, the mix manifold 250, or any portion of a looped flow path for recirculating cabin air 252.

Figure 3:
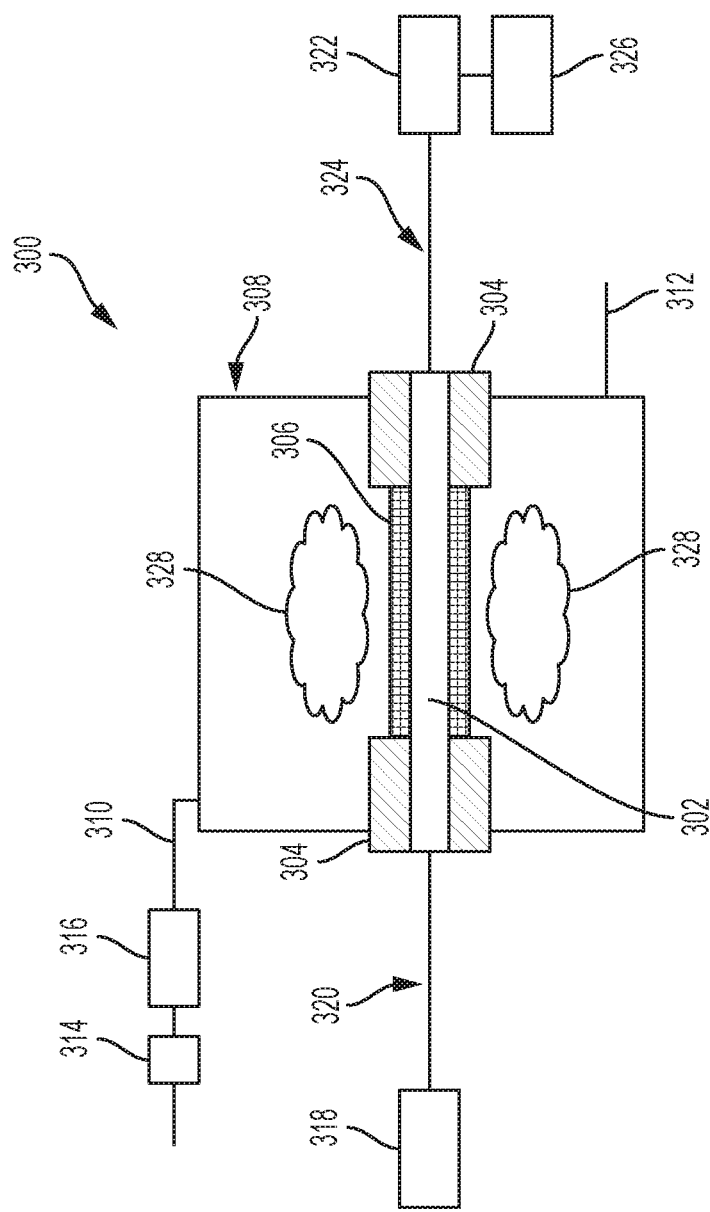
FIG. 3 is a schematic depiction of a contaminant sensor.

An example embodiment of a contaminant sensor assembly 300 is schematically shown in FIG. 3. As shown in FIG. 3, an optical guide in the form of a fiber optic element shown in a cross-sectional view with a fiber optic element core 302 and a fiber optic element cladding 304 around the core 302.

The core and cladding can be made of various types of glass or plastic with high transmissivity and appropriate refractive indices to guide light within the core axially along the length of the fiber. This is accomplished with a refractive index differential at the interface along which the core is optically coupled to the cladding such that light transmitting through the core that is incident on the interface totally reflected back into the core according to Snell's Law. This phenomenon is known as total internal reflection, and is the basis for fiber optic technology, camera and binocular prisms, automotive windshield rain sensors, and numerous other technologies. A portion of the fiber optic element has a layer comprising a metal organic framework (MOF) 306 instead of cladding on the surface of the core 302.

Metal organic framework materials are well-known in the art, and comprise metal ions or clusters of metal ions coordinated to organic ligands to form one-, two- or three-dimensional structures. A metal-organic framework can be characterized as a coordination network with organic ligands containing voids. The coordination network can be characterized as a coordination compound extending, through repeating coordination entities, in one dimension, but with cross-links between two or more individual chains, loops, or spiro-links, or a coordination compound extending through repeating coordination entities in two or three dimensions. Coordination compounds can include coordination polymers with repeating coordination entities extending in one, two, or three dimensions. Examples of organic ligands include but are not limited to bidentate carboxylates (e.g., oxalic acid, succinic acid, phthalic acid isomers, etc.), tridentate carboxylates (e.g., citric acid, trimesic acid), azoles (e.g., 1,2,3-triazole), as well as other known organic ligands. Metal organic frameworks are further described by Batten, S R; Champness, N R; Chen, X-M; Garcia-Martinez, J; Kitagawa, S; Öhrström, L; O'Keeffe, M; Suh, M P; Reedijk, J (2013). "Terminology of metal-organic frameworks and coordination polymers (IUPAC Recommendations 2013)", Pure and Applied Chemistry. 85 (8): 1715. doi:10.1351/PAC-REC-12-11-2, the disclosure of which is incorporated herein by reference in its entirety.

A wide variety of metals can be included in a metal organic framework. In some embodiments, the metal organic framework comprises a transition metal, including but not limited to any of the transition metals described above with respect to transition metal oxide adsorbents. Examples of metals that can be included in the metal organic framework include Cu, Mg, Cr, Al, Mn, Co,Zr Zn. Lanthanide metals can include Ln, Eu, Ce, Er. Examples of specific metal organic framework materials include UIO-66 Zr-bdc, UiO-66-NH$_2$ ({Zr(bdc-NH$_2$)$_2$} with (bdc-NH$_2$)=2-amino-1, 4-benzenedicarboxylate)), UIO-67 (Zr-bpdc) with bpdc=biphenyl-4,4'-dicarboxylic acid), MIL-101 ([Cr$_3$(O)X (bdc)$_3$(H$_2$O)$_2$] (X=OH or F) with bdc=1,4-benzene dicarboxylate), NU-1000 ({Zr$_6$($\mu_3$—OH)$_8$(—OH)$_8$(TBAPy)$_2$ with TABAPy=1,3,6,8,-tetrakis(p-benzoic-acid)pyrene)), PCN-777 ({[Zr$_6$(O)$_4$(OH)$_{10}$(H$_2$O)$_6$(TATB)$_2$ with TATB=4, 4',4"-s-triazine-2,4,6-triyl-tribenzoate),MOF-808 Zr$_6$O$_4$ (OH)$_4$(BTC)$_2$(HCOO)$_6$ with BTC=1,3,5-benzenetricarboxylate), MOF-200 and MOF-210 [Zn$_4$O(BBC)$_2$ and (Zn$_4$O)$_3$(BTE)$_4$(BPDC)$_3$, respectively; BBC=4,4',4"-(benzene-1,3,5-triyl-tris (benzene-4,1-diyl))tribenzoate; BTE=4, 4',4"-(benzene-1,3,5-triyl-tris(ethyne-2,1-diyl)) tribenzoate; BPDC=biphenyl-4,4'-dicarboxylate], MOF-177 [Zn$_4$O (BTB)2; BTB=4,4',4"-benzene-1,3,5-triyl-tribenzoate], [MOF-399, Cu3(BBC)2] with BBC3-=4,4',4"-(benzene-1,3, 5-triyl-tris(benzene-4,1-diyl))tribenzoate. MOF's can be synthesized by hydrothermal or solvothermal techniques, where crystals are slowly grown from a hot solution. Templating for the MOF structure can be provided by a secondary building unit (SBU) and the organic ligands. Alternate synthesis techniques are also available, such as chemical vapor deposition, in which metal oxide precursor layers are deposited followed by exposure of the precursor layers to sublimed ligand molecules to impart a phase transformation to the MOF crystal lattice.

In some embodiments, the MOF 306 can be configured to promote absorption or adsorption of target contaminant(s). For example, tricresyl phosphate is commonly used as an anti-wear or anti-corrosion additive in hydraulic fluids used on aircraft. Tricresyl phosphate is toxic and has a low vapor pressure, which can make it a problematic contaminant for aircraft pressurized air, even at low concentrations. In some embodiments, the MOF 306 can be configured to deter absorption or adsorption of potential cross-contaminants (i.e., compounds that could produce a false positive) by the MOF 306. For example, the MOF can include functional groups appended to metal or organic portions of the framework that can attract or otherwise interact the contaminant(s). The MOF can also be configured with a porosity adapted for adsorption of the contaminant(s). In the case of testing for TCP, the pore size of the MOF 306 should be larger than at least 1.5 nm, as the TCP molecule kinetic diameter is larger than 1.5 nm. In some embodiments, the MOF can include pore sizes from 1.5 nm to 4 nm. Polar groups can be included in the MOF 306 to attract or otherwise interact with polar contaminants such as tricresyl phosphate. Examples of polar substituent groups that can be included in the MOF 306 can include hydroxyl, carbonyl, carboxyl, amino. In some embodiments, the MOF 306 can be immobilized in a polymer matrix in order to increase the sensitivity of the target analyte. In some embodiments, metal oxides (e.g., zinc oxide, iron oxide, titania, vanadium oxide) can be incorporated within the pore system of MOF 306 for enhanced selectivity of the target analyte. In some cases, metal nanoparticles (e.g., gold, platinum, palladium, copper, and nickel) can be impregnated in the pore system of MOF 306 to enhance the selectivity of the target analyte.

With reference again to FIG. 3, the portion of the fiber optic element with the metal organic framework 306 is disposed inside of a flow cell 308 equipped with an inlet 310 and an outlet 312. The inlet 310 receives an air sample from an air source such as one of the locations mentioned above (e.g., ECS conduit 245, FIG. 2), and can optionally be equipped with supplemental equipment such as a sampling pump or fan 314 or a heater 316. The core 302 is optically connected on one end to a light source 318 (e.g., a laser at a wavelength, e.g., a near-infrared (NIR) laser, that is absorbed by the contaminant but not by other likely components of the gas sample). The light source 318 is connected to the core 302 through an optical connection 320. The optional connection 320 can be any type of optical connection such as a fiber optic cable extension of the fiber optic element in the flow cell 308, or a direct connection of the light source 318 to the fiber optic element in the flow cell 308. The core 302 is optically connected on another end to a light detector 322 through an optical connection 324, which can be the same or different type of optical connection as the optical connection 320. An electronic processing unit 326 is shown connected to read the output of the light detector 322, and can be operationally connected (e.g., through wired connections (not shown) or through wireless connections) to other system components such as the light source 318, the sampling pump or fan 314 or the heater 316, or to other on-board systems and operational structures.

During operation, sampled air is introduced to the flow cell 308 through the inlet 310. In the presence of a contaminant 328 such as tricresyl phosphate, the contaminant 328 is adsorbed by the MOF 306 to concentrate the contaminant molecules at the interface with the fiber optic core 302, where the contaminant molecules provoke a change of the evanescent field of traveling light in the fiber optic core 302, which in turn impacts signal intensity as well as spectral changes in the light received by light detector 322. Elution of bound contaminant molecules can be carried out by exposing the MOF 306 to a heat source such as directing air heated by heater 316 (e.g., 80° C.) into the flow cell 308. In some embodiments, the electronic processing unit 326 can generate a response (or can engage with a master system controller to generate a response), including but not limited to providing a system alarm to the presence of the contaminant, reducing a flow rate of compressed outside air to the air cycle machine, or increasing a recirculation flow rate in the aircraft pressurized zone.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the spirit and scope of the present disclosure. Additionally, while various embodiments of the present disclosure have been described, it is to be understood that aspects of the present disclosure may include only some of the described embodiments. Accordingly, the present disclosure is not to be seen as limited by the foregoing description, but is only limited by the scope of the appended claims.

What is claimed is:

1. An aircraft pressurized air system, comprising:
   a compressor that receives and compresses outside air;
   an air cycle machine that receives compressed air from the compressor and directs conditioned air to an aircraft pressurized zone; and
   a contaminant sensor disposed along an air flow path between the compressor and the aircraft pressurized zone, comprising an optical guide, a metal organic framework on an exterior surface of the optical guide in operative fluid communication with air from the air flow path, a light source in communication with the optical guide at a first end of the optical guide, and a light detector in communication with the optical guide at a second end of the optical guide.

2. The system of claim 1, wherein the optical guide comprises a fiber optic element including a core comprising an optical material with a first refractive index, said metal organic framework on a first exterior surface portion of the core, and a cladding optically coupled to a second exterior surface portion of the core, said cladding comprising an optical material with a second refractive index lower than the first refractive index and configured to reflect light from the core at an interface between the core and the cladding.

3. The system of claim 2, further comprising a filament, wherein the first exterior surface portion is disposed at a central portion along a length of the filament, and the cladding disposed on each side of the central portion along the length of the filament.

4. The system of claim 1, wherein the metal organic framework is configured to adsorb tricresyl phosphate.

5. The system of claim 4, wherein the metal organic framework includes pore sizes greater than a molecular kinetic diameter of the tricresyl phosphate.

6. The system of claim 4, wherein the metal organic framework includes functional groups interactive with tricresyl phosphate.

7. The system of claim 1, wherein the metal organic framework includes pores larger than 1.5 nm.

8. The system of claim 1, wherein the metal organic framework includes polar functional groups.

9. The system of claim 1, further comprising a heat source in controllable thermal communication with the metal organic framework for regeneration.

10. The system of claim 1, further comprising a controller configured to detect a contaminant based on output from the contaminant sensor, and to generate a response thereto.

11. The system of claim 10, wherein the response is selected from:
    providing a system alarm to the presence of the contaminant, reducing a flow rate of compressed outside air to the air cycle machine, increasing a recirculation flow rate in the aircraft pressurized zone, or activating an air contaminant removal protocol.

12. A method of providing pressurized air to an aircraft pressurized zone, comprising:
    compressing outside air via a compressor;
    directing compressed outside air to an air cycle machine that receives conditioned air for delivery to the aircraft pressurized zone; and
    testing air on an air flow path between the compressor and the aircraft pressurized zone with a sensor comprising an optical guide, a metal organic framework on an exterior surface of the optical guide in operative fluid communication with air from the air flow path, a light source in communication with the optical guide at a first end of the optical guide, and a light detector in communication with the optical guide at a second end of the optical guide.

13. The method of claim 12, wherein the metal organic framework is configured to adsorb tricresyl phosphate.

14. The method of claim 12, further comprising generating a response based on detection of a contaminant.

15. The method of claim 14, wherein the response is selected from: providing a system alarm to the presence of the contaminant, reducing a flow rate of compressed outside air to the air cycle machine, or increasing a recirculation flow rate in the aircraft pressurized zone.

16. The method of claim 14, further comprising regenerating the metal organic framework with heated air.

* * * * *